US008167928B2

(12) United States Patent
Melzer et al.

(10) Patent No.: US 8,167,928 B2
(45) Date of Patent: May 1, 2012

(54) MRT-COMPATIBLE VALVE PROSTHESIS FOR USE IN THE HUMAN OR ANIMAL BODY FOR REPLACEMENT OF AN ORGAN VALVE OR A VESSEL VALVE

(75) Inventors: Andreas Melzer, Taunesstein (DE); Erwin Immel, Gelsenkirchen (DE)

(73) Assignee: Vueklar Cardiovascular Ltd., Stirling (GB)

( * ) Notice: Subject to any disclaimer, the term of this patent is extended or adjusted under 35 U.S.C. 154(b) by 204 days.

(21) Appl. No.: 12/066,810

(22) PCT Filed: Sep. 14, 2006

(86) PCT No.: PCT/EP2006/008964
§ 371 (c)(1),
(2), (4) Date: Mar. 13, 2008

(87) PCT Pub. No.: WO2007/031316
PCT Pub. Date: Mar. 22, 2007

(65) Prior Publication Data
US 2008/0249611 A1    Oct. 9, 2008

(30) Foreign Application Priority Data
Sep. 14, 2005  (DE) .......................... 10 2005 044 009

(51) Int. Cl.
*A61F 2/06* (2006.01)
(52) U.S. Cl. ...................... 623/1.24; 623/1.15; 600/410
(58) Field of Classification Search .................. 324/318; 219/635; 600/421, 423, 410, 431; 623/1.1, 623/1.15, 1.44, 1.24, 1.22, 2.1–2.42
See application file for complete search history.

(56) References Cited

U.S. PATENT DOCUMENTS
6,280,385 B1 *  8/2001  Melzer et al. ................. 600/423
6,767,360 B1     7/2004  Alt et al.
(Continued)

FOREIGN PATENT DOCUMENTS
EP          1092985         4/2001
(Continued)

OTHER PUBLICATIONS

International Search Report prepared by the European Patent Office on Nov. 27, 2006 for PCT/EP2006/008964; Applicant, Biophan Europe GmbH.

(Continued)

*Primary Examiner* — Brian Pellegrino
*Assistant Examiner* — Matthew Schall
(74) *Attorney, Agent, or Firm* — Jason H. Vick; Sheridan Ross, PC (57) ABSTRACT

The invention relates to a biological or artificial valve prosthesis (4, 5) for use in the human or animal body for replacement of an organ valve or a vessel valve, in particular a cardiac valve prosthesis or venous valve prosthesis, with a stent (8) or without a stent, with a supporting valve framework, with at least one valve (7) and with at least one conductor loop (2) that forms the inductance of an electrical resonance circuit. In order to provide a simple and inexpensive valve prosthesis that can be viewed in the MR imaging technique and is also easy to implant, the invention proposes that the at least one conductor loop (2) forms the valve framework and/or the valve (7) or supporting areas of the valve framework and/or supporting areas of the valve (7).

22 Claims, 9 Drawing Sheets

U.S. PATENT DOCUMENTS

| | | | |
|---|---|---|---|
| 6,847,837 B1 * | 1/2005 | Melzer et al. | 600/421 |
| 7,279,664 B2 * | 10/2007 | Weber | 219/635 |
| 2005/0049692 A1 * | 3/2005 | Numamoto et al. | 623/1.24 |
| 2008/0262628 A1 * | 10/2008 | Laitenberger et al. | 623/23.7 |

FOREIGN PATENT DOCUMENTS

| | | | |
|---|---|---|---|
| WO | WO 9919739 A1 * | 4/1999 | |

OTHER PUBLICATIONS

International Preliminary Report on Patentability (including translation) prepared by the International Bureau on Apr. 8, 2008 for PCT/EP2006/008964; Applicant, Biophan Europe GmbH.

Written Opinion prepared by the European Patent Office on Nov. 27, 2006 for PCT/EP2006/008964; Applicant, Biophan Europe GmbH.

* cited by examiner

MRT-COMPATIBLE VALVE PROSTHESIS FOR USE IN THE HUMAN OR ANIMAL BODY FOR REPLACEMENT OF AN ORGAN VALVE OR A VESSEL VALVE

CROSS REFERENCE TO RELATED APPLICATION

This application is a national stage application under 35 U.S.C. 371 of PCT Application No. PCT/EP2006/008964 having an international filing date of Sep. 14, 2006, which designated the United States, which PCT application claimed the benefit of German Application Serial No. 10 2005 044 009.6, filed Sep. 14, 2005, the entire disclosure of each of which is hereby incorporated herein by reference.

The invention relates to a biological or artificial valve prosthesis for use in the human or animal body for the replacement of an organ valve or a vessel valve, in particular a cardiac valve prosthesis or venous valve prosthesis, with a stent or without a stent, with a supporting valve framework, with at least one valve and with at least one conductor loop which forms the inductance of an electrical resonance circuit.

Biologically speaking, venous valves are located in the deep leg veins. They serve to prevent the backflow of the venous blood into the limbs. Through compression of the veins during the tensing of the muscles, the blood is transported in the direction of the heart. The valves can become leaky (insufficient) or lose their function through the accumulation of coagulated blood (leg vein thrombosis). Venous valve prostheses are currently under development and generally consist of a stent framework made of self-expanding material such as, for example, nitinol or a steel framework into which either a valve made of polymer or a thin film of nitinol or a metal mesh. The valve function can optionally be restored surgically through the installation of a woven sleeve with narrowing of the veins.

The cardiac valves are located inside of the heart and separate the atria from the ventricles and ensure, as one-way valves, that the blood flows in the correct direction. The heart has four valves, of which two belong to the right and two belong to the left heart. The blood flows out of the venous vessels into the atrium or the auricle, from there through a valve into the ventricle and from there, in turn, through a valve into the vessels of the systemic or pulmonary circulation. The cardiac valves consist of thin, stable layers of connective tissue which are formed in the manner of pockets (aortic valve and pulmonary valve) or sails (mitral valve and tricuspid valve). Like the rest of the heart's interior, they are covered by the thin interior skin of the heart (endocardium).

In the case of considerable restriction of the valve function as a result of inborn or acquired defects such as valve insufficiency or valve stenosis, the replacement of the cardiac valve with a prosthesis is necessary. There are two types of cardiac valve prostheses, namely the biological and mechanical cardiac valve. The biological cardiac valves are also called stentless valve prostheses, since they do not contain a stabilizing framework. The valves are prepared from pig heart valves or from the tissue of the bovine pericardium or the submucosa of the small intestines of pigs or from human endothelial cells on collagen fibers or plastic or metal nets/films cultivated according to the shape and function of the human cardiac valve. In most cases, these prostheses do not necessitate lifelong administration of oral anticoagulant to thin the blood but rather only a temporary anticoagulant in the first few months after the operation.

Mechanical valves consist of metal and/or plastic. They require lifelong anticoagulation but have an almost unlimited service life. The valves are encased by a woven sleeve with which they are stitched into the position of the former defective cardiac valve.

Operations for the replacement of defective cardiac valves are performed in heart surgery under induced (cardioplegic, diastolic) cardiac arrest in order to achieve a blood-free, calm operation situs. In this state, a wide variety of types of cardiac valves are stitched in place. As compensation for this cardiac arrest, it is first necessary to maintain circulation using a heart-lung machine, and the main artery (aorta) must also be clamped off. These measures are associated with significant side effects and complications.

Current developments are consequently aimed in the direction of an implantation of collapsible cardiac valve prostheses which are inserted and placed via catheter. The basis of the prostheses is a stent-like framework into which either a biological valve or a polymer valve is fitted. The implantation is performed by means of balloon dilation or self-expansion. However, it is disadvantageous that the stent frameworks of the collapsible, known cardiac valve prostheses impair MRT visualization and hence interfere with a very simple check of the valve function.

A percutaneously implantable cardiac valve prosthesis can significantly reduce the risk that is present during an open operation; however, the precise positioning of an X-ray control is not possible, since the soft tissue of the heart is not represented and only appears through the administration of contrast medium through the perfused area. An implantation through MRT imaging would be advantageous, since both the flowing blood and the heart tissue are represented without contrast medium.

According to current state of the art, the collapsible cardiac valves currently available on the market do not yet have optimal characteristics, given that the function of the implants can be controlled only to a limited extent and only invasively through the use of catheters, X-ray radiation and contrast media with considerable risks and burdens for the patients and the medical personnel. Both during the placement of the implant and during the required follow-up examinations, long periods of fluoroscopy are often necessary. They last between 10 and 15 minutes but can reasonably last for 60 minutes or more. Side effects such as the development of radiation abscesses (ulceration) can result from the long exposure periods, which can lead to skin cancer. The long periods of fluoroscopy and correspondingly high dose levels have also resulted in radiation damage suffered by patients who have been subjected to a cardiac intervention. The Federal Department of Radiation Protection has determined in this regard that the reduction of the exposure to radiation in medical diagnosis is of considerable significance.

Examination techniques using magnetic resonance tomography (MRT) can contribute significantly to the reduction of examination procedures involving X-ray diagnosis and nuclear medicine. In addition to the lack of radiation exposure, magnetic resonance tomography has other advantages in comparison to X-ray techniques such as computer tomography and fluoroscopy. It offers an outstanding soft tissue contrast and is the only layered imaging technique that offers completely free layer positioning. Spatially resolved spectrometric techniques allow for a functional analysis of biochemical processes in the human body. Likewise, vessels can be represented directly in the operation area without the use of contrast media. In open magnetic resonance tomography, the physician has access to the patient and, as a result, can perform aspiration and operations under direct MRT control. Catheterizations can also be performed well in closed high-field devices with modern imaging.

A cardiac valve prosthesis of the type mentioned at the outset is already known from EP 1 092 985 A2, from which the MR imaging technique is also derived, to which express reference is made here. The known cardiac valve prosthesis has an external valve framework on which the actual cardiac valve is movably supported. Both coils and capacitors are provided on the annular supporting framework to form the resonant circuit. Of advantage in the known cardiac valve prosthesis is that it can be represented outstandingly using the MR imaging technique. A disadvantage is that this prosthesis cannot be implanted percutaneously.

While conventional collapsible cardiac valves can be implanted percutaneously, imaging in magnetic resonance tomographs currently has the following considerable disadvantages:
- a pronounced tendency toward interference and artifacts due to the metals used,
- due to the Faraday cage effect, the insides of a metal implant are shielded and observable only with difficulty,
- metal- or plastic-based valve mechanisms either do not provide a signal or lead to magnetic field inhomogenization,
- in the moved metal components of the valve mechanism in the strong magnetic field, undesired inductive effects can occur,
- the biological valves consist predominantly of collagen fibers that provide no signal or only a weak one, and few cells, so that direct MRT imaging is impeded,
- the temporal and spatial resolutions are insufficient for the complete diagnosis of the valve and its functions.

As a consequence of the aforementioned problems, conventional collapsible cardiac valves, which usually consist of stainless steel alloys or nitinol, are not usable or only insufficiently usable for MRT examinations of the valve functions and the correct positions of the prosthesis.

It is therefore the object of the present invention to make available a valve prosthesis of the type mentioned at the outset in which the aforedescribed disadvantages are avoided.

The aforementioned object is achieved according to the invention in a valve prosthesis in that the at least one conductor loop forms the valve framework and/or the valve and/or supporting areas of the valve framework and/or supporting areas of the valve of the prosthesis. The arrangement according to the invention offers a series of significant advantages, with the at least one conductor loop assuming a plurality of functions. First, the conductor loop forms the MR resonant circuit and thus ensures the MR function. Moreover, the conductor loop forms the valve framework or at least supporting areas of the valve framework for the mounting of the valve. Moreover, the conductor loop can also form the valve or supporting areas of the valve. Since the conductor loop assumes a supporting function in the prosthesis according to the invention, it is also possible to keep the throughput opening of the prosthesis open by means of the conductor loop. Finally, an anchoring or fastening function results especially if the conductor loop additionally comprises anchoring means.

Preferably, a provision is made in the invention that the stent and/or the valve framework has cells of varying sizes on its exterior, which is to say on the external circumferential casing surface. Resulting is a lattice or net arrangement on the exterior, with it then being possible to provide a plurality of uniformly-sized as well as differently-sized cells or openings or windows.

Moreover, due to the fact that the conductor loop forms the valve framework, it is quite easily possible to design the prosthesis to be completely collapsible or expandable and hence percutaneously implantable.

Finally, the invention consequently results in a valve prosthesis comprising at least one closed resonant circuit with an inductance and preferably a capacitance which is percutaneously implantable in collapsible arrangement, with an optimal stabilization and anchoring of the prosthesis being achieved by means of the resonant circuit construction and geometry. Here, the electrical resonance circuit generates a signal response which is detected and represented in a spatially resolved manner by means of at least one external reception coil, so that the MR imaging of the valve and of its function is improved. Moreover, the valve prosthesis according to the invention is particularly well-suited to implanting under MR imaging, since the opening as well as the positioning and anchoring can be determined precisely.

To anchor the conductor loop or the resonant circuit, it is expedient to provide anchoring means, for example in the form of eyelets, hooks or the like. In this connection, it is favorable to embody the anchoring means in one piece with the conductor loop, so that no further components are necessary for anchoring. However, it is also possible in principle to design the eyelets, hooks or the like as separate components which are then immovably fastened to the coil wire. In connection with the anchoring means, it is important that they not protrude in the compressed state of the valve prosthesis over same and, if the valve prosthesis is located at the site of implantation, become active and can be used to fasten the prosthesis to the surrounding tissue only after opening. Through the integration and immediate proximity of the anchoring to the resonant circuit, improvement is achieved particularly of the correct positioning of the prosthesis under MRT as well as the subsequent diagnosis with respect to leakiness of the valve site.

The present invention is notably suitable in connection with biological, stentless valve prostheses, particularly heterologous ones from an animal, such as the cardiac valve or the pericardium of a pig or the pericardium of a cow, or homologous and isologous ones from human tissues and cells, with the conductor loop being enclosed in these cases by the biological cardiac valve. Finally, in this case the biological cardiac valve contains the conductor loop and hence the resonant circuit. As will readily be understood in this context, the conductor loop has a shape which is adapted to the natural cardiac valve, with the valve shoulders or leaves being encompassed in at least one coil and the base of the cardiac valve being enclosed by a cylinder coil.

Particularly in connection with a biological cardiac valve, it is expedient that bioresorbable components which stabilize and seal off the valve prosthesis for implantation be provided. Here, the at least one conductor loop is then provided for implantation in a biological component of the valve prosthesis and remains there after the bioresorbable components have been broken down in the body. The bioresorbable components therefore merely serve to stabilize the valve prosthesis up to the time immediately following the implantation. However, the ingrown cardiac valve continues to have advantageous characteristics for MRT imaging in order to be able to represent optimally in the MRT defects occurring over the long term, such as wear and tissue reaction, and to initiate a treatment or a replacement in a timely manner.

While it is possible in principle to design the prosthesis without a stent, it goes without saying that prostheses with a stent are also possible. In this case, a provision is then made according to the invention that the valve framework and the valve are fixed by the conductor loop at least in part in a self-opening or mechanically, particularly hydraulically or fluidly, expandable stent such that, during compression and subsequent opening, both the valve framework and the valve as well as the conductor loop return to the desired shape, position and geometry, hence simultaneously achieving the necessary sealing-off of the prosthesis in its bed. In this connection, it is particularly preferred that the entire mechanism not only be held by the conductor loop but that the conductor loop also serve to fasten the valve on the stent. Here, at least areas of the conductor loop are then drawn out of the stent. These areas can also be used for anchoring in the surrounding tissue and hence constitute an anchoring means.

Preferably, a provision can be made that the framework forms several resonant circuits with different resonant frequencies, each with a conductor loop, or that several resonant circuits are coupled to each other with only one conductor loop. In this manner, not only is the supporting function of the valve framework improved, but the cardiac valve replacement can consequently also be used in different MRTs. It is preferred in this connection that the valve framework have several different coil shapes, i.e. different coil geometries such as, for example, cylinder, saddle and bird cage coils.

In addition, at least one coil of the resonant circuit can also have a meander structure. It is also advantageous if the conductor loop or the conductor web itself is embodied to be meander-shaped. Resulting from this embodiment is a targeted and defined collapsibility and expansion, with the surface of the coil being increasable and the elasticity in the bed tissue being improved. At the same time, fatigue failures can be combated with this embodiment.

Since the shape of the conductor loop can be selected at will, it is expedient that, in a biological cardiac valve, the conductor loop have the shape of a natural cardiac valve and at least two loops of the conductor loop be provided which form a cylindrical shape with their surfaces, enclose the natural valve shape and keep the outlets of the coronary vessels open in the area between the loops.

In order to obtain a compact prosthesis, it is expedient that the additional capacitor belonging to the resonant circuit be fastened or arranged on and/or in the valve prosthesis and/or integrated into the design of the valve prosthesis.

Here, in connection with the anchoring, the inductance and/or capacitance of the resonant circuit is provided at least in part for integration into the tissue enclosing the valve prosthesis for the purpose of stitching on, anchoring, and/or sealing.

In order to set the external parasitic capacitance, the conductor loop is coated with a nonconductor as a dielectric layer, particularly with plastic and/or ceramic. In this manner, the desired parasitic capacitance can be set on the one hand by way of the selection and technique of the coating and on the other hand by way of the thickness of the coating, which is at least 1 nanometer. Moreover, through the dielectric layer and the spacing between the loops of the at least one conductor loop, an internal capacitance is formed whose magnitude can be adjusted through the type of dielectric layer and the spacing of the individual loops.

Here, the outer coating or dielectric layer preferably consists of Teflon, polyester, polyurethane, parylene or other suitable polymers. Besides the insulating function and the formation of the parasitic and internal capacitance, the dielectric layer can have the additional task of attaching or fixing another coil belonging to the resonant circuit and/or at least one capacitance on or in the framework of the prosthesis.

In addition, it can also be expedient to attach or fix the conductor loop or coil on the valve framework or the valve prosthesis by means of a layer. Accordingly, the valve prosthesis or the valve framework can be coated with an appropriate material.

Finally, the resonant circuit of the cardiac valve prosthesis according to the invention is embodied such that the resonant circuit has a resonant frequency, particularly in the high-frequency range, namely in the range between 8 to 400 MHz, which corresponds to the frequency of an external magnetic field, particularly of an MR tomography.

In principle, a provision can be made that the conductor loop be manufactured from a wire or a tube or from sheet metal cut from a material with a low magnetic susceptibility such as, for example, nitinol or a good electric conductivity such a noble metal or a noble metal alloy or from a material with a low magnetic susceptibility and a good electric conductivity such as, for example, tantalum. Alternatively, however, it is also possible that the conductor loop have a nonconductive conductor support which is coated with a conductive material, particularly gold, platinum, tantalum and/or conductive alloys. In addition, however, it is also possible that the conductor support be conductive and coated with an appropriate material in order to improve its electrical conductivity. It is favorable to implement the conductor loop through the coating of the valve prosthesis with a conductive material. Preferably, the application of the coating occurs by means of vapor deposition or sputtering (PVD or CVD).

A low magnetic susceptibility is present in materials which have a dielectric constant of much greater than 1. Accordingly, for example, the dielectric constant of the magnetic susceptibility of nitinol lies at $3 \cdot 10^6$. By contrast, materials with a good electrical conductivity in [S/m] have values which are much greater than 1. Thus, the electrical conductivity of titanium is $2.34 \cdot 10^6$ S/m, whereas that of copper is between 35 to $58 \cdot 10^6$ S/m.

In connection with the application of the coating, it is expedient particularly with polymers, ceramic, nickel titanium and titanium as the material of the conductor support to apply a base layer onto this material in order to improve the adhesion of the coating. The base layer is then ultimately an adhesion promoter.

In addition to the aforedescribed parasitic and/or internal capacitance, it is expedient, incidentally, that an additional capacitance be implemented by means of a capacitor. Consequently, it is then not necessary to implement special shapes or special coatings of the conductor loop in order to achieve prescribed internal and parasitic capacitances.

In order to facilitate the implantation and in order to be able to monitor both the opening and the function of the valve prosthesis according to the invention, a provision is made in a collapsible and expandable valve prosthesis that it is designed such that, during expansion, the resonant frequency is changed by changing the coil geometry of the resonant circuit and can be set to the resonant frequency of the MR tomograph.

The present invention further relates to a percutaneously implantable and expandable biological or artificial valve prosthesis for use in the human and/or animal body for the replacement of an organ valve or vessel valve, with at least one valve mechanism provided with a valve and with a stent with a casing made of biocompatible material, with the stent being enclosed at the functional height of the valve by at least one conductor loop which forms the inductance of an electrical resonance circuit.

In contrast to the aforedescribed form of embodiment, the valve prosthesis itself or the valve framework or even the valve is not formed by the conductor loop. In this embodiment, the resonant circuit is fixed around the stent at the functional height of the valve in the form of the at least one conductor loop.

In the aforementioned embodiment, there are various fundamental alternatives with respect to the arrangement of the conductor loop. On the one hand, the conductor loop can be arranged around the supporting framework of the stent. However, since the supporting framework of the stent can impair the MR function, it is particularly expedient, on the other hand, that the supporting framework of the stent or supporting areas of the stent framework be formed by the conductor loop. A negative influence of the resonant frequency by a second supporting framework cannot occur in this case. Moreover, it is possible that the conductor loop serve to attach the valve mechanism in the stent and be at least partially drawn out of the stent for this purpose. Finally, an anchoring of the stent in the valve support can be achieved by means of the conductor loop or commensurate anchoring means of the conductor loop. Here, too, the conductor loop of course has multiple functions as well.

In connection with the aforedescribed embodiment with stent, it goes without saying that the valve prosthesis here can have all of the aforementioned features that have been described previously in the valve prosthesis named at the outset independently or in combination.

Finally, the present invention relates to an MRT technique in which an altered signal response is generated in a locally limited area within and/or outside the valve prosthesis by means of a closed resonant circuit with an inductance whose resonant frequency is substantially equal to the resonant frequency of the directed high-frequency radiation and in which the range with an altered signal response detected by at least one reception coil is represented in a temporally and spatially resolved manner using respiratory triggering and/or ECG triggering.

The aforementioned method facilitates the temporal resolution and controlling of the acquisition of the patient to be treated after ECG and respiratory triggering.

In the following, sample embodiments of the invention are explained on the basis of the drawing.

Figure 1:
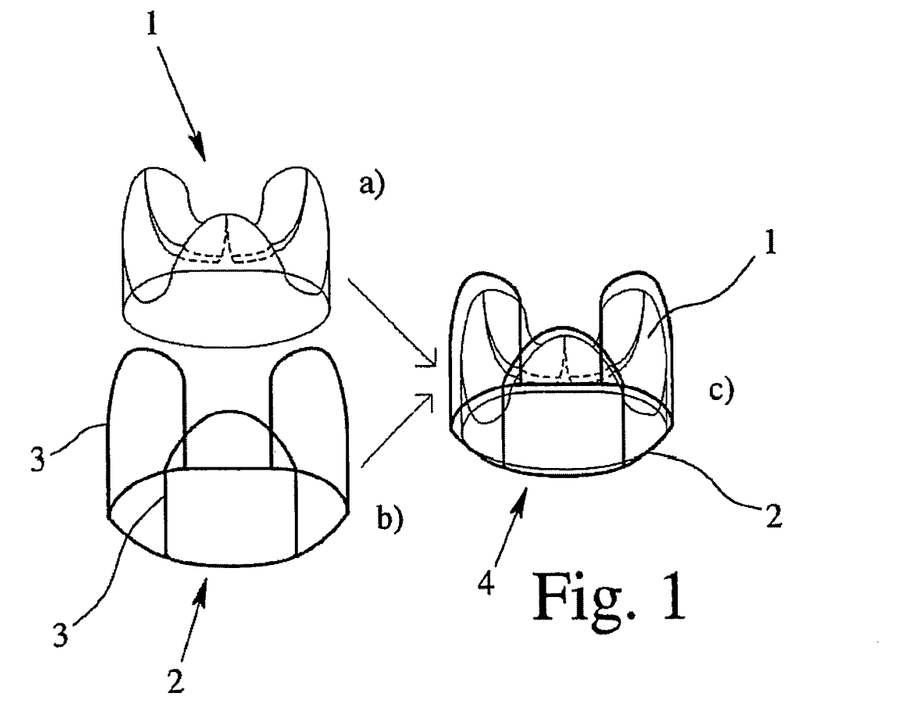
FIG. 1 shows a perspective, schematic view of a biological valve prosthesis.

Depicted in diagram a of FIG. 1 is a biological cardiac valve 1. The type and design of the biological cardiac valve 1 is in itself known. Shown in diagram b is a conductor loop 2 which forms the inductance of an electrical resonance circuit and hence the resonant circuit as such. A comparison of diagrams a and b of FIG. 1 makes it clear that the conductor loop 2, as a closed conductor web, forms three loops 3 which are arranged together in the shape of a cylinder. The loops 3 of the conductor loop 2 are adapted to the shape of the biological cardiac valve 1.

Diagram c from FIG. 1 shows the biological valve prosthesis 4, wherein the conductor loop 2 or the resonant circuit is integrated into the biological cardiac valve or the biological cardiac valve 1 is inserted into the conductor loop 1 [sic]. It is not shown in detail that the conductor loop 2 has at least one capacitance.

Figure 2:
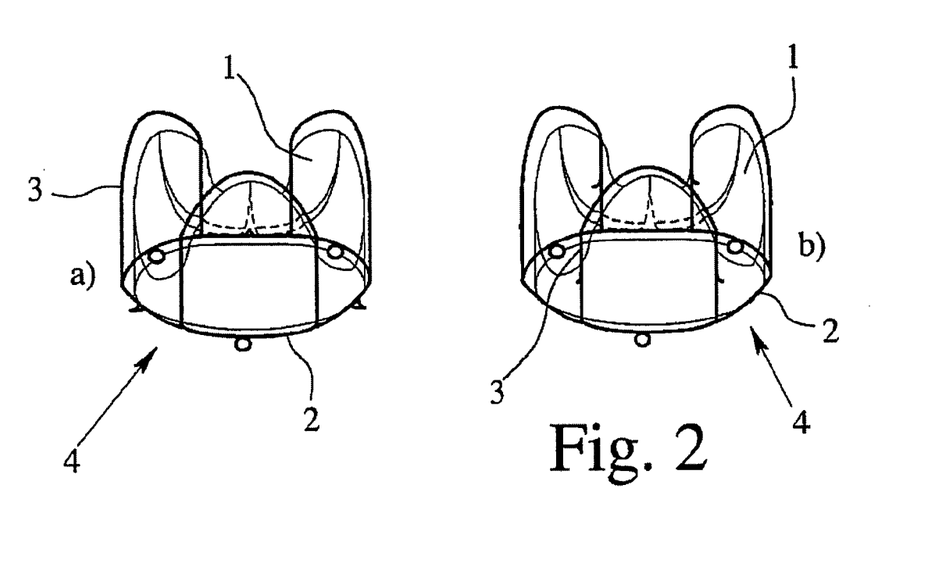
FIG. 2 shows a perspective, schematic view of other embodiments of biological valve prostheses.

The valve prostheses 4 depicted in FIG. 2 differ from the valve prosthesis 4 depicted in FIG. 1c) in that anchoring means are provided in the form of eyelets and hooks. In the embodiment according to FIG. 2a), hooks and eyelets are located only on the circumferential annular area of the conductor loop 2, whereas in the embodiment according to FIG. 2b), anchoring means present in the form of hooks are also provided on the loops.

Also not shown is that the cardiac valve prosthesis can also have only two loops instead of three loops in order to be adapted in this way to a double atrioventricular valve.

Moreover, it goes without saying that the anchoring means depicted in FIG. 2, for example in the form of hooks and/or eyelets, can be implemented in all of the conductor loops portrayed in the following, even if this is not presented in detail.

Figures 3, 4:
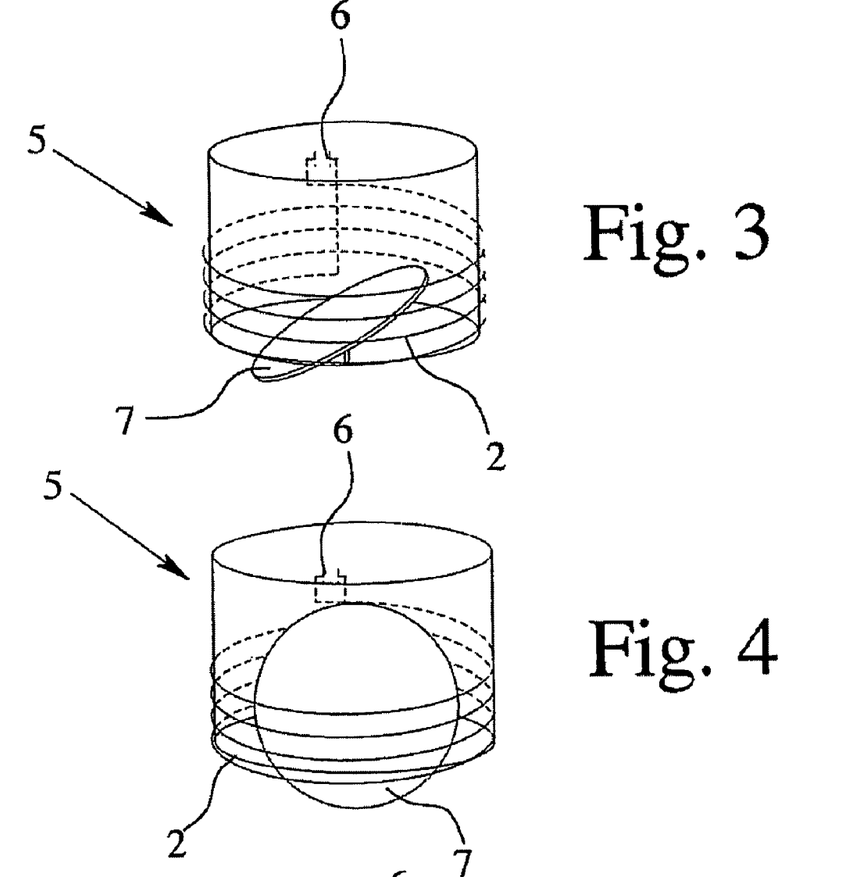
FIG. 3 shows a perspective, schematic view of an artificial valve prosthesis with a valve designed as a cap on the base of a solenoid coil.
FIG. 4 shows a view corresponding to FIG. 3 of a valve prosthesis with a valve designed as a sphere.

Depicted in FIG. 3 is an artificial valve prosthesis 5 with a conductor loop 2 on the basis of a solenoid coil. The resonant circuit here has a capacitance 6. The artificial valve prosthesis 5 has a valve 7 designed as a cap. In the sample embodiment shown, the conductor loop 2 forms the supporting valve framework of the valve prosthesis 5. In this connection, it should be pointed out that the individual representations are merely schematic, diagram-like illustrations of the respective valve prostheses 4, 5.

The artificial valve prosthesis 5 depicted in FIG. 4 corresponds to the valve prosthesis 5 depicted in FIG. 3, but with a sphere provided as a valve 7.

Figure 5:
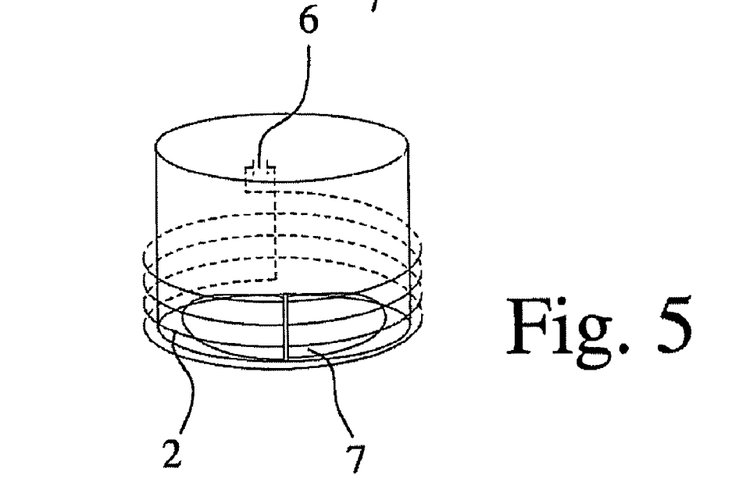
FIG. 5 shows a view corresponding to FIG. 3 of a valve prosthesis with a valve designed as a double valve.

The artificial valve prosthesis 5 depicted in FIG. 5 also corresponds to the valve prosthesis 5 depicted in FIG. 3, but with a double valve according to the double valve principle, which is referred to as double-leaf valve in the following, provided as a valve 7.

Figure 6:
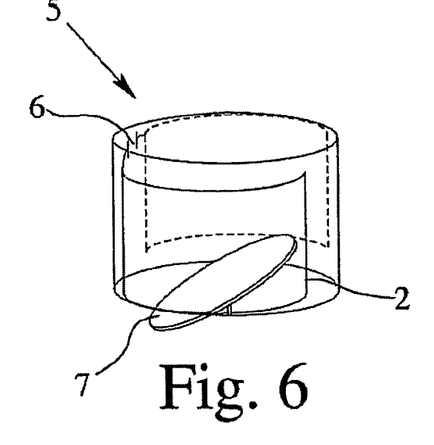
FIG. 6 shows a perspective, schematic view of an artificial valve prosthesis with a valve designed as a cap on the basis of a saddle coil.

The valve prosthesis 5 depicted in FIG. 6 corresponds substantially to the valve prosthesis 5 depicted in FIG. 3, but with a saddle coil provided instead of a solenoid coil.

Figure 7:
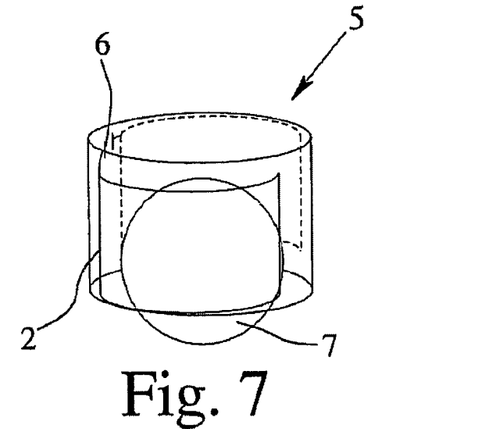
FIG. 7 shows a view corresponding to FIG. 6 of an artificial valve prosthesis with a valve designed as a sphere.

The valve prosthesis 5 depicted in FIG. 7 corresponds to that depicted in FIG. 6, but with a sphere provided as a valve 7.

Figure 8:
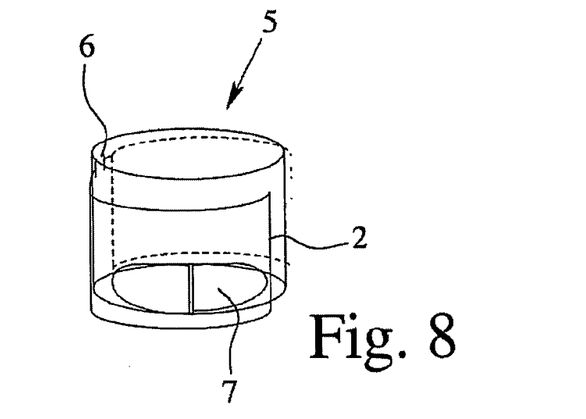
FIG. 8 shows a view corresponding to FIG. 6 of an artificial valve prosthesis with a valve designed as a double valve.

The valve prosthesis 5 depicted in FIG. 8 corresponds to that depicted in FIG. 6, but with a double valve provided as a valve 7.

Figure 9:
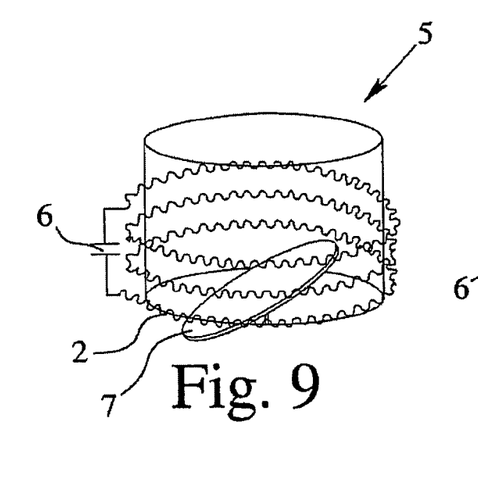
FIG. 9 shows a perspective, schematic view of an artificial valve prosthesis with a valve designed as a cap on the basis of a solenoid coil with a meander-shaped conductor loop.

The artificial valve prosthesis 5 depicted in FIG. 9 is an integrated resonant circuit on the basis of a solenoid coil, as also follows from FIG. 3. In contrast to the embodiment according to FIG. 3, the conductor loop 2 is designed to have a meander shape. The meander shape of the conductor wire makes it possible in an especially simple manner to collapse the valve prosthesis 5.

Figure 10:
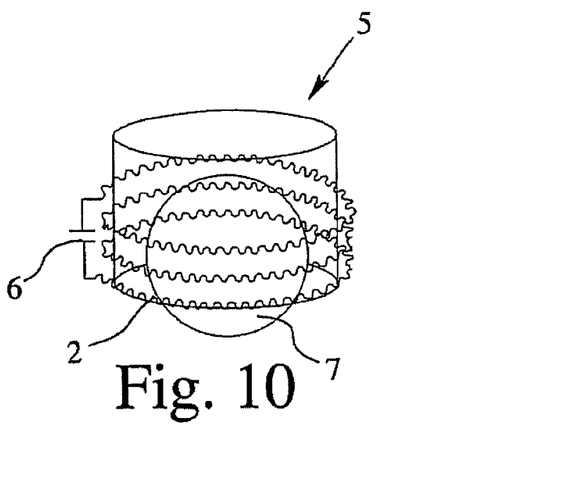
FIG. 10 shows a view corresponding to FIG. 9 of an artificial valve prosthesis with a valve designed as a sphere.
Figure 11:
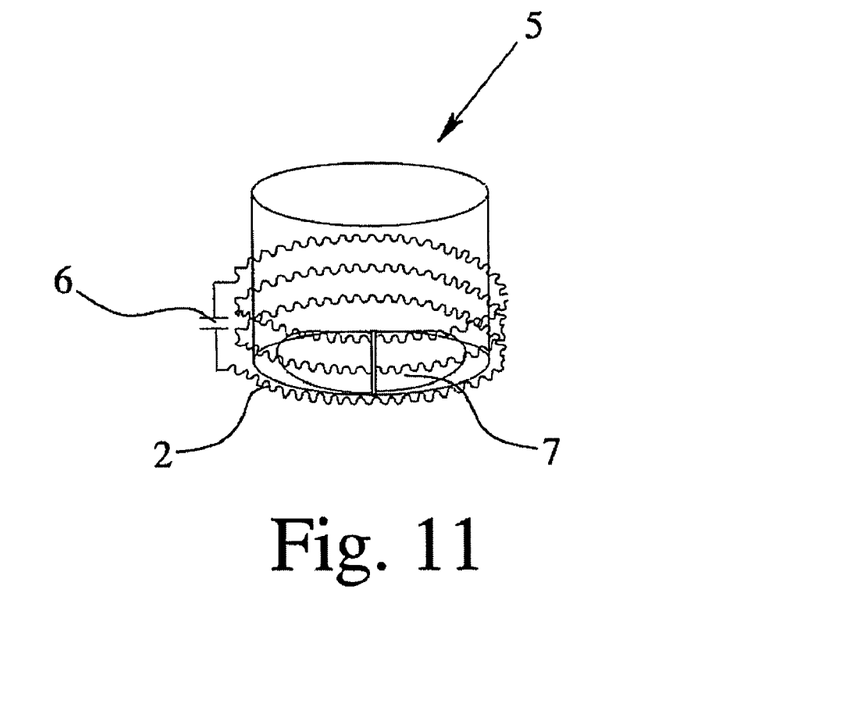
FIG. 11 shows a view corresponding to FIG. 9 of an artificial valve prosthesis with a valve designed as a double valve.

The embodiment according to FIG. 10 corresponds to the embodiment according to FIG. 6, but with a sphere provided as a valve 7. In the embodiment shown in FIG. 11, in contrast to the embodiment depicted in FIG. 10, a double valve is provided instead of the sphere.

Figure 12:
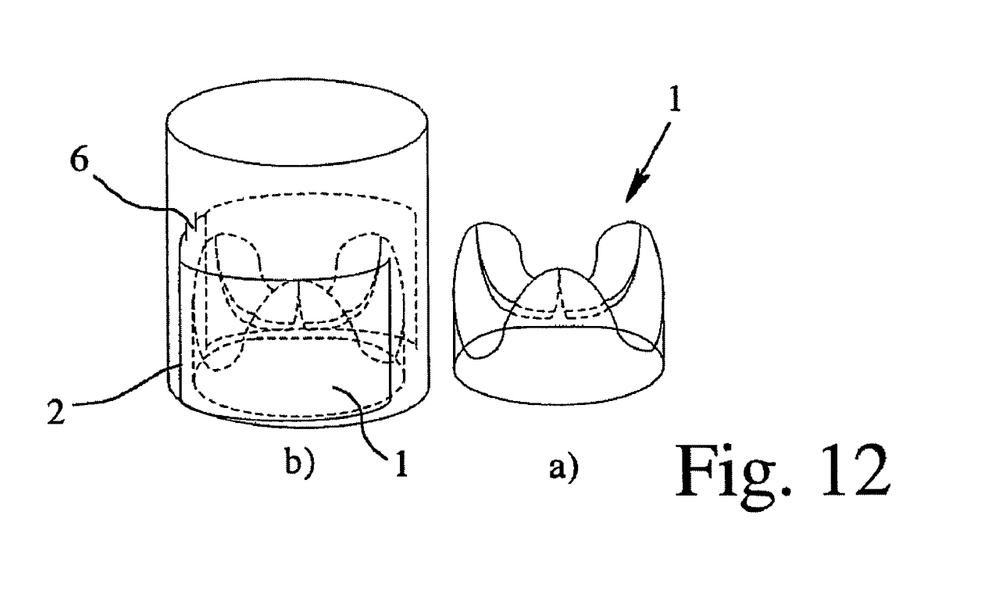
FIG. 12 shows a perspective, schematic view of a biological valve prosthesis in a stent with a saddle coil.

Shown in FIG. 12 in diagram a is a biological cardiac valve 1. As follows from diagram b, the cardiac valve 1 is integrated into a stent 8. In addition, a conductor loop 2 embodied as a saddle coil and having a capacitance 6 is provided as support for the cardiac valve 1 and hence as a framework for the cardiac valve 1. The height of the conductor loop 6 corresponds to the height of the cardiac valve 1, so that all relevant areas are able to be covered by way of the conductor loop 2. Moreover, it will readily be understood that, in addition to the saddle coil, another conductor loop 2 can be provided, which is depicted in FIG. 1b. Here, the individual coils can be formed from different conductor loops 2 or from a single conductor loop 2.

Figure 13:
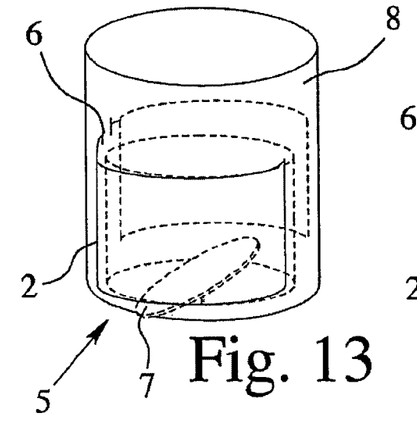
FIG. 13 shows a perspective, schematic view of an artificial valve prosthesis in a stent with a saddle coil.
Figure 14:
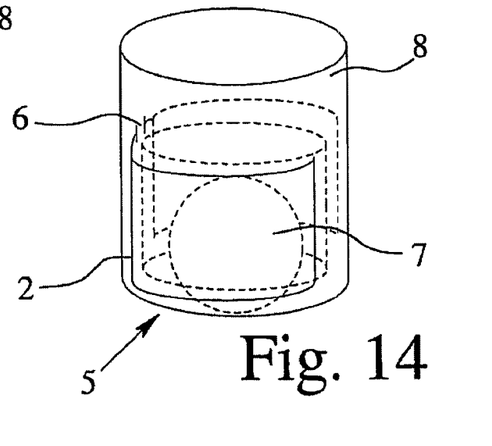
FIG. 14 shows a perspective, schematic view of an artificial valve prosthesis in a stent with a valve designed as a sphere.
Figure 15:
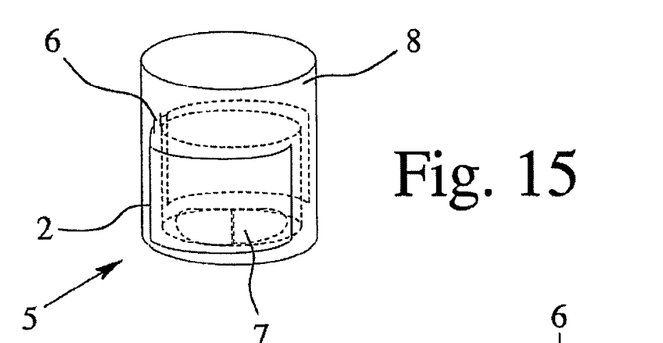
FIG. 15 shows a view corresponding to FIG. 13 of an artificial valve prosthesis with a valve designed as a double valve.

The embodiments of FIGS. 13 through 15 correspond substantially to the embodiment of FIG. 12, with the embodiments depicted in FIGS. 13 through 15 being artificial valve prostheses 5 which are arranged in a stent 8. The respective conductor loop 2 is designed as a saddle coil and arranged inside the stent 8. The conductor loop 2 respectively forms the support of the valve prosthesis 5, with a valve being provided in the form of a cap in the embodiment according to FIG. 13, in the form of a sphere in the embodiment according to FIG. 14 and in the form of a double valve in the embodiment according to FIG. 15.

Represented in each of FIGS. 16 to 23 are embodiments in which the respective valve prosthesis 4, 5 has a stent 8 into which a biological cardiac valve 1 or an artificial cardiac valve 9 is integrated as a valve mechanism. In each case, the stent 8 has a sleeve made of a biocompatible material. In addition, the stent 8 is enclosed at the functional height of the respective valve of at least one conductor loop 2 which forms the inductance of an electrical resonance circuit. In all of the embodiments here as well as in all aforedescribed embodiments, the height of the respective coil or the height extension of the conductor loop is such that a relevant coil field results such that the respective valve is also substantially completely enclosed during the function. The ratio of the diameter of the prosthesis opening to the height of the respective coil lies between 4:1 to 0.5:1.

FIGS. 16 to 23 are also merely schematic representations. The following options are possible in all of the depicted embodiments:

1. The stent 8 has a separate supporting framework (not shown) which spreads the stent 8 and holds it open. The conductor loop 2 is arranged on the outside around the sleeve of the stent 8 and the supporting framework in the area of the cardiac valve.
2. The conductor loop 2 forms at least a portion of the supporting framework or supporting areas of the framework of the stent 8. Here, the conductor loop 2 then assumes not only function of the resonant circuit but rather also the framework function of the stent.
3. The conductor loop 2 is not only wound around the stent 8 in the relevant area, but also serves to attach the biological cardiac valve 1 or the artificial cardiac valve 9. Finally, the cardiac valve 1, 9 is stitched as a valve mechanism to the conductor loop 2 or parts of the conductor loop 2. In this case, the conductor loop 2 assumes the additional function of attaching the cardiac valve 1, 9 inside the sleeve of the stent 8. Here, outwardly facing areas of the conductor loop 2 can then have hooks, eyelets or other anchoring means in order to facilitate the attachment of the stent 8 to the site of implantation.
4. Moreover, it is possible to combine two or three of the aforementioned possibilities. Accordingly, the conductor loop 2, in addition to alternative 3, can also carry out the function of the stent 8 as supporting framework at least in the relevant area of the cardiac valve 1, 9.

Figure 16:
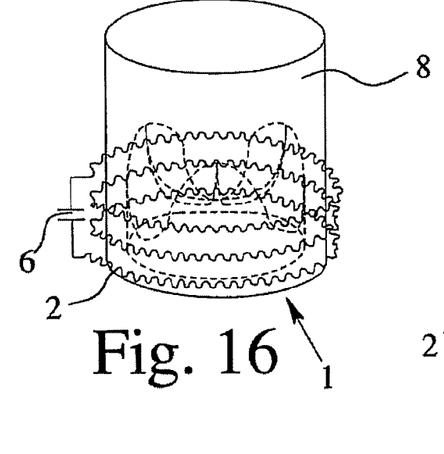
FIG. 16 shows a perspective, schematic view of a biological valve prosthesis with a stent and an external solenoid coil made of an electrically conductive material formed into a meander.
Figure 17:
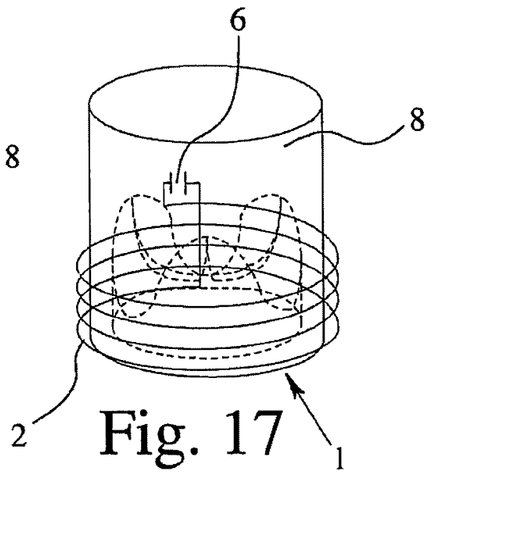
FIG. 17 shows a perspective, schematic view of a biological cardiac valve in a stent with an external cylinder coil.

FIGS. 16 and 17 each show a biological cardiac valve 1 which is placed into the stent 8. In the embodiment according to FIG. 16, a solenoid coil with a meander-shaped conductor loop 2 is located in the relevant area, i.e. in the area of the cardiac valve 1, whereas the coil is embodied as a cylinder coil in the embodiment according to FIG. 17.

Figure 18:
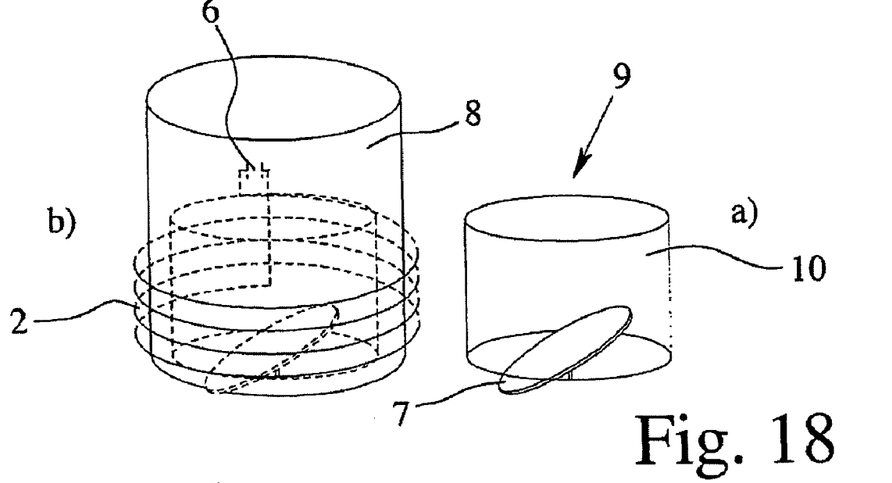
FIG. 18 shows a perspective, schematic view of an artificial valve prosthesis with a stent and an external cylinder coil and a valve designed as a cap.

Provided in the embodiment depicted in FIG. 18 is an artificial cardiac valve 9 which has a support 10 which serves to position the valve 7, which is represented in FIG. 18a. In the diagram according to FIG. 18b, the artificial cardiac valve 9 is placed into the stent 8, with the conductor loop 2 forming a cylinder coil with capacitance 6.

Figure 19:
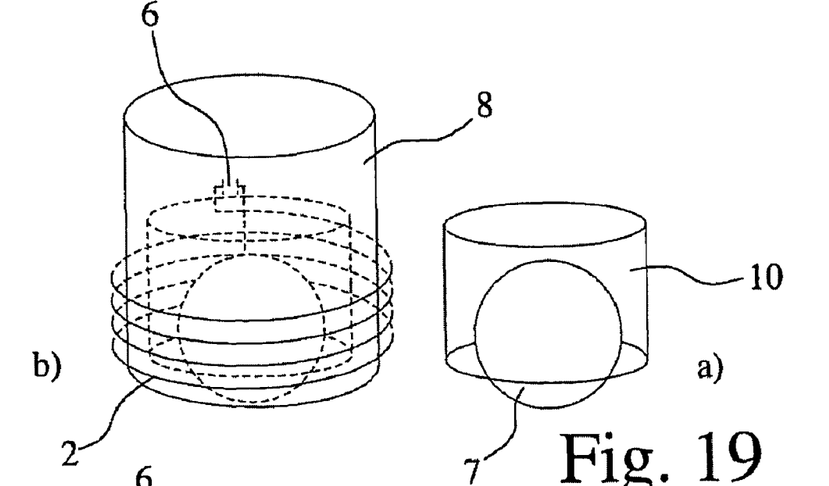
FIG. 19 shows a view corresponding to FIG. 18 of an artificial valve prosthesis with a valve designed as a sphere.
Figure 20:
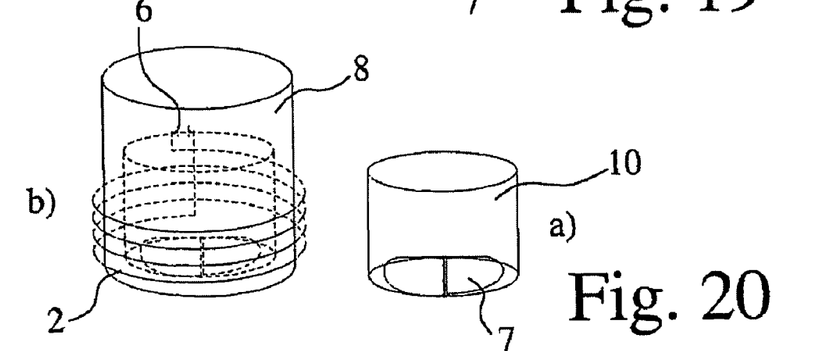
FIG. 20 shows a view corresponding to FIG. 18 of an artificial valve prosthesis with a valve designed as a double valve.

The embodiment depicted in FIG. 19 corresponds substantially to the embodiment depicted in FIG. 18, with a sphere provided as a valve 7. By contrast, in the embodiment depicted in FIG. 20, a double valve is provided as a valve 7.

Figure 21:
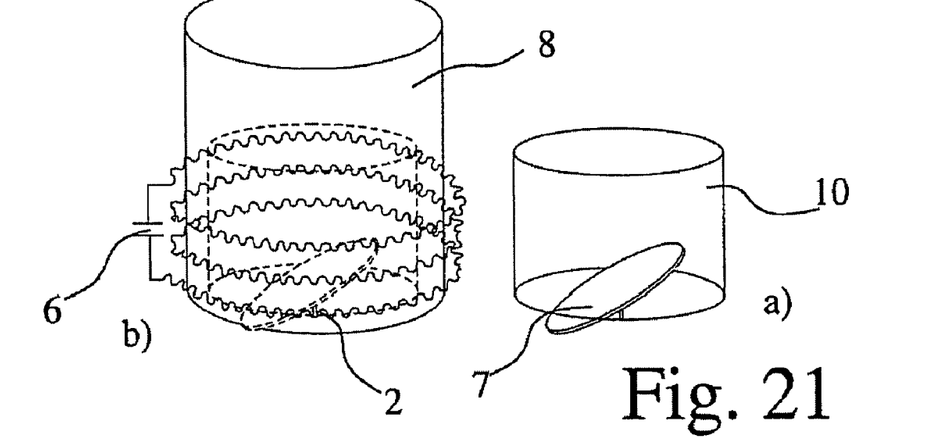
FIG. 21 shows a perspective, schematic view of an artificial valve prosthesis in a stent with an external solenoid coil made of an electrically conductive material formed into a meander and a valve designed as a cap.

The embodiment depicted in FIG. 21 corresponds to the embodiment depicted in FIG. 18, but the conductor loop 2 is embodied as a solenoid coil and the conductor web 2 is embodied as such in a meander shape.

Figure 22:
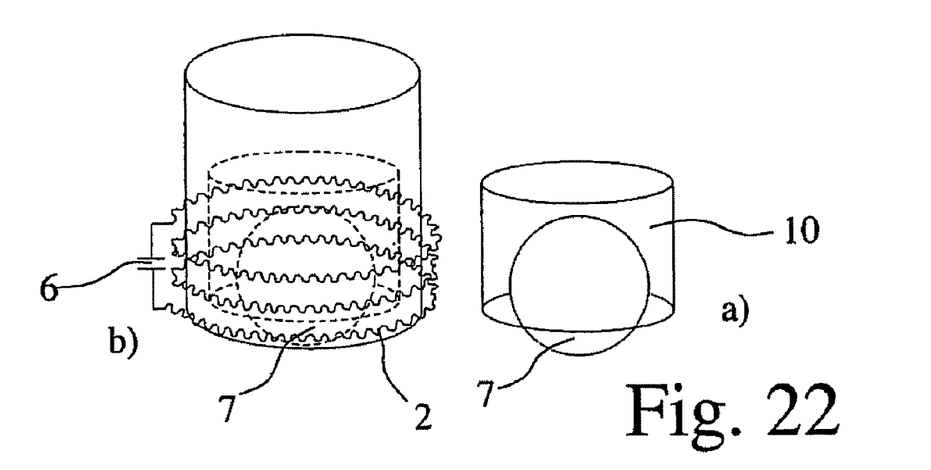
FIG. 22 shows a view corresponding to FIG. 21 of an artificial valve prosthesis with a valve designed as a sphere, FIG. 23 a view corresponding to FIG. 21 of an artificial valve prosthesis with a valve designed as a double valve.
Figure 23:
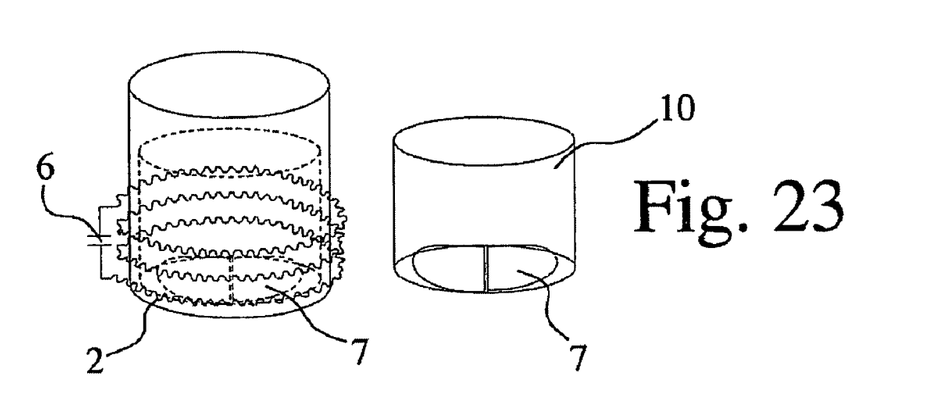

While a cap is provided as a valve 7 in the embodiment according to FIG. 21, a sphere is provided as a valve in the embodiment according to FIG. 22. By contrast, in the embodiment according to FIG. 23, a double valve is provided as a valve. There are otherwise no differences between the embodiments according to FIGS. 21, 22 and 23.

Figure 24:
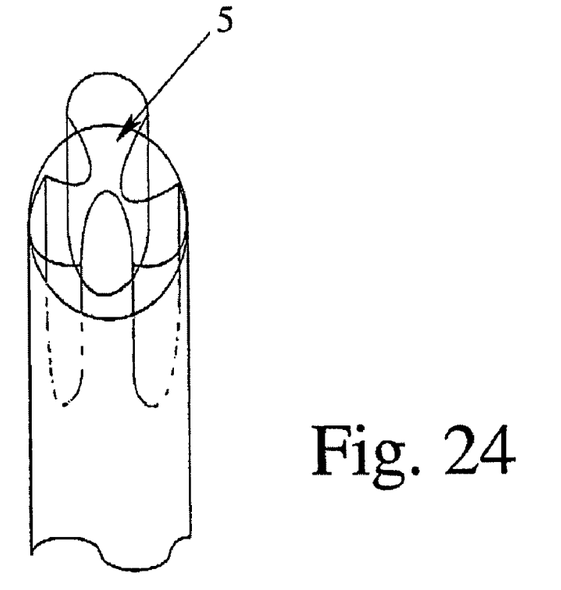
FIG. 24 shows a schematic view of a valve prosthesis arranged in a catheter.
Figure 25:
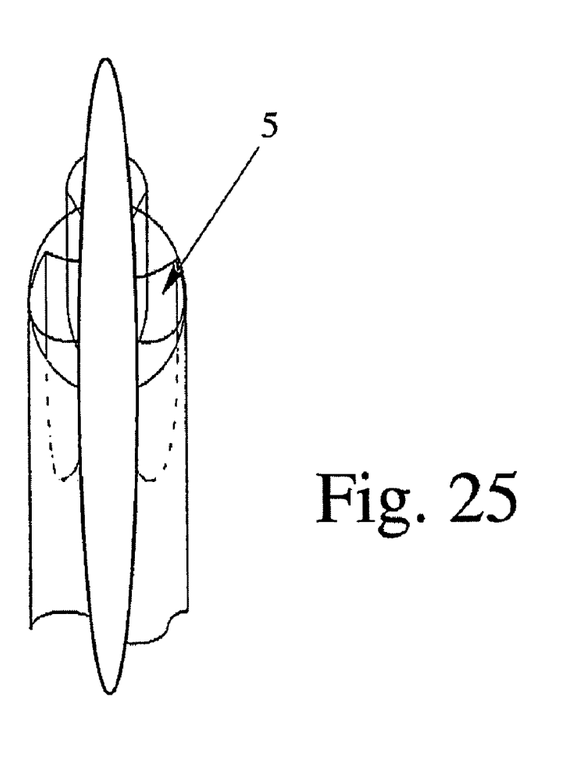
FIG. 25 shows a schematic view of a valve prosthesis which can be expanded with a balloon.

In FIGS. 24 and 25, the insertion of a valve prosthesis 5 according to the invention is represented schematically. The valve prosthesis 5 depicted in FIG. 24 is a self-expanding prosthesis which expands automatically after arrangement in the site of implantation and withdrawal of the catheter holding the prosthesis in the collapsed state. By contrast, the prosthesis 5 of the embodiment depicted in FIG. 25 is expanded by means of a balloon that is arranged inside the prosthesis. To this end, the prosthesis is placed in the site of implantation using a shuttle catheter which is subsequently withdrawn. After withdrawal of the catheter, the prosthesis initially does not open up. The opening-up is brought about through the expansion of the balloon. To this end, an appropriate medium is fed to the balloon. After expansion, the balloon is pulled out of the prosthesis.

Figure 26:
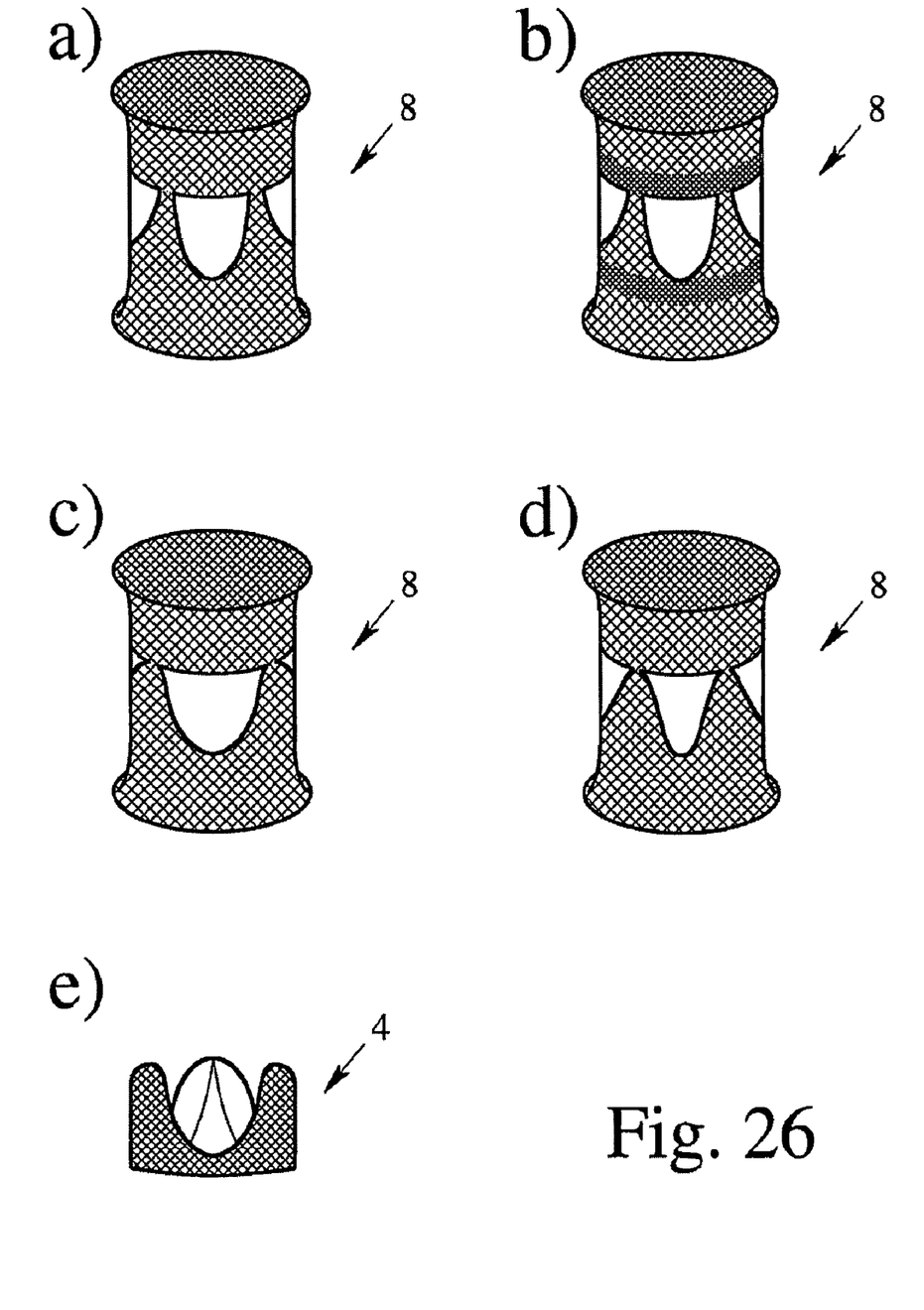
FIG. 26 shows various representations of stents and valve prostheses of cell-equivalent or different size.

FIG. 26 shows embodiments of valve prostheses according to the invention. Here, embodiments a), b), c) and d) each show a stent 8, with the external circumferential casing surface of the stent 8 having a lattice or net structure and having a plurality of cells of the same and of different sizes. In principle, the cells, which can also be referred to as windows or openings, can have any shape.

In the embodiment according to FIG. 26a, two types of cells are provided, namely predominantly small cells and, in the middle area, larger, approximately triangular-shaped cells.

The embodiment according to FIG. 26b differs from the embodiment according to FIG. 26a in that three types of cells of different sizes are provided. Located respectively above and below the larger middle cells is a strip with very small cells.

In the embodiment according to FIG. 26c, the middle cells are relatively large. Only three large cells are provided.

The embodiment according to FIG. 26d corresponds substantially to the embodiment according to FIG. 26c, but more than three large middle cells are provided.

FIG. 26e shows a valve prosthesis (4) which corresponds substantially to the valve prosthesis according to FIG. 1c, but a plurality of small cells is provided on the outside.

What is claimed is:

1. A biological or artificial valve prosthesis for use in a human or animal body for the replacement of a valve, with a supporting valve framework, with at least one valve and with conductor loops forming the inductance of an electrical resonance circuit,
    wherein the conductor loops form solely the valve framework and are the only structure forming the framework and assuming a supporting function in the prosthesis,
    wherein the capacitance belonging to the resonant circuit is integrated into the design of the valve prosthesis,
    wherein the at least one conductor loop is at least partially coated with a nonconductor as a dielectric layer,
    wherein at least one internal capacitance is formed by the dielectric layer and the spacing between the loops of the conductor loops, and
    wherein the electrical resonance circuit generates a signal response, which is detectable and representable in a spatially resolved manner by means of at least one external reception coil, so that MR imaging of the valve and of its function is improved.

2. The valve prosthesis as set forth in claim 1, wherein the valve framework has on its outside a plurality of cells of one of a same size and a different size.

3. The valve prosthesis as set forth in claim 1, wherein the valve prosthesis is collapsible, expandable and percutaneously implantable.

4. The valve prosthesis as set forth in claim 1, wherein anchoring means are provided on one or more of the conductor loop and the valve framework.

5. The valve prosthesis as set forth in claim 1, wherein the anchoring means do not protrude over the valve prosthesis in the compressed state and only become active after opening.

6. The valve prosthesis as set forth in claim 1, wherein a biological stentless cardiac valve, particularly from an animal such as pig (cardiac valve, pericardium) or from a cow (pericardium) or from human tissues and cells, is enclosed by at least one conductor loop.

7. The valve prosthesis as set forth in claim 1, wherein bioresorbable components which stabilize the valve prosthesis for the implantation are provided, and that the at least one conductor loop is provided for implantation in a biological component of the valve prosthesis and remains there after the bioresorbable components have been broken down in a body.

8. The valve prosthesis as set forth in claim 1, wherein the valve framework and the valve are fixed by the conductor loop at least in part in a self-opening or mechanically expandable stent such that, during compression and subsequent opening, both the valve framework and the valve as well as the conductor loop return to a desired shape, position and geometry and sealing-off of the prosthesis in its bed.

9. The valve prosthesis as set forth in claim 1, wherein the valve framework forms:
    several resonant circuits each with a conductor loop, or
    several resonant circuits with different resonant frequencies and only one conductor loop coupled to each other.

10. The valve prosthesis as set forth in claim 1, wherein at least one coil of the resonant circuit has collapsible geometries, crossed conductor loops or a meander structure and the conductor web of the conductor loop is embodied in a meander shape.

11. The valve prosthesis as set forth in claim 1, wherein the conductor loop has the shape of a biological cardiac valve, and that at least two loops of the conductor loop are provided which form a cylinder shape with their surfaces, which enclose the natural valve shape in the shape of a loop and keep the outlets of the coronary vessels open in the area between the loops.

12. The valve prosthesis as set forth in claim 1, wherein the capacitance belonging to the resonant circuit is one or more of:
    attached and fixed on the valve prosthesis,
    attached and fixed in the valve prosthesis, and
    integrated into the design of the valve prosthesis.

13. The valve prosthesis as set forth in claim 1, wherein the conductor loops are attached to or fixed on a second valve framework of the valve.

14. The valve prosthesis as set forth in claim 1, wherein the valve prosthesis is collapsible and openable and is embodied such that, upon opening, the resonant frequency is changed as a result of the change in the coil geometry of the resonant circuit and can be set to the resonant frequency of a MR tomograph, so that the opening process during the implantation can be monitored via a change of signal characteristic in an MR image.

15. The valve prosthesis as set forth in claim 1, wherein the valve is an organ valve or a vessel valve.

16. The valve prosthesis as set forth in claim 15, wherein the organ valve is a cardiac valve prosthesis and the vessel valve is a venous valve prosthesis.

17. The valve prosthesis as set forth in claim 1, wherein the valve prosthesis includes a stent.

18. The valve prosthesis as set forth in claim 1, wherein the valve prosthesis does not include a stent.

19. The valve prosthesis as set forth in claim 4, wherein the anchoring means are one or more of eyelets and hooks.

20. The valve prosthesis as set forth in claim 19, wherein the anchoring means are designed in one piece with the conductor loop.

21. The valve prosthesis as set forth in claim 8, wherein the expandable stent is one or more of hydraulically and fluidly expandable.

22. A biological or artificial valve prosthesis for use in a human or animal body for the replacement of a valve, with a supporting valve framework, with at least one valve and with conductor loops forming the inductance of an electrical resonance circuit, wherein the conductor loops solely forms the valve, wherein the capacitance belonging to the resonant circuit is integrated into the design of the valve prosthesis, wherein the at least one conductor loop is at least partially coated with a nonconductor as a dielectric layer, and wherein at least one an internal capacitance is formed by the dielectric layer and the spacing between the loops of the conductor loops, and wherein the electrical resonance circuit generates a signal response, which is detectable and representable in a spatially resolved manner by means of at least one external reception coil, so that the MR imaging of the valve and of its function is improved.

* * * * *